United States Patent [19]
Henrick et al.

[11] 3,995,054
[45] Nov. 30, 1976

[54] CONTROL OF ACARINA BY ESTERS OF CYCLOPROPANE ACIDS

[75] Inventors: Clive A. Henrick; Gerardus B. Staal, both of Palo Alto, Calif.

[73] Assignee: Zoecon Corporation, Palo Alto, Calif.

[22] Filed: June 11, 1975

[21] Appl. No.: 585,988

Related U.S. Application Data

[60] Division of Ser. No. 461,189, April 12, 1974, Pat. No. 3,925,460, which is a continuation-in-part of Ser. No. 413,958, Nov. 8, 1973, abandoned, Ser. No. 367,058, June 4, 1973, abandoned, Ser. No. 390,991, Aug. 23, 1973, abandoned, Ser. No. 350,952, April 13, 1973, Pat. No. 3,849,466, and Ser. No. 351,028, April 13, 1973, Pat. No. 3,860,629.

[52] U.S. Cl. ............................ 424/305; 424/DIG. 12
[51] Int. Cl.$^2$ .......................................... A01N 9/24
[58] Field of Search ..................... 424/305, DIG. 12; 260/468 H

[56] References Cited
UNITED STATES PATENTS

| | | |
|---|---|---|
| 3,236,728 | 2/1966 | Newallis et al. ............... 424/305 |
| 3,683,005 | 8/1972 | Sota et al. ..................... 260/468 H |
| 3,925,460 | 12/1975 | Henrick et al. ................ 260/468 H |
| 3,925,461 | 12/1975 | Henrick et al. ................ 260/468 H |

Primary Examiner—V. D. Turner
Attorney, Agent, or Firm—Donald W. Erickson

[57] ABSTRACT

Methods and compositions for the control of Acarina employing esters of cyclopropane carboxylic acids described herein.

61 Claims, No Drawings

CONTROL OF ACARINA BY ESTERS OF CYCLOPROPANE ACIDS

This is a division of application Ser. No. 461,189, filed Apr. 12, 1974, now U.S. Pat. No. 3,925,460, which is a continuation-in-part of applications Ser. No. 413,958, filed Nov. 8, 1973, now abandoned; Ser. No. 367,058, filed June 4, 1973, now abandoned; Ser. No. 390,991, filed Aug. 23, 1973, now abandoned; Ser. No. 350,952, filed Apr. 13, 1973, now U.S. Pat. No. 3,849,466; and Ser. No. 351,028, filed Apr. 13, 1973, now U.S. Pat. No. 3,860,629, the disclosures of which are incorporated by reference herein.

This invention relates to novel compounds, synthesis thereof, compositions thereof, and the control of mites.

The compounds of the present invention are effective for the control of mites and especially spider mites. Spider mites are plant feeders and cause serious damage to orchard trees, field crops, greenhouse plants and other vegetation. They feed on the foliage and fruit of plants and trees and attack a variety of plants and trees due to their wide distribution. Spider mites of the family Tetranychidae, such as *Tetranychus urticae*, *Tetranychus canadensis*, *Tetranychus cinnabarinus*, *Tetranychus pacificus*, *Bryobia praetiosa*, *Oligonychus pratensis*, *Oligonychus ilicis*, *Panonychus citri*, *Panonychus ulmi*, and similar related species, are of particular biological interest and economic importance. Other mites are those of the family Tarsonemidae, such as *Steneotarsonemus pallidus*.

Compounds of the present invention of the following formulas I and II are effective control agents for mites.

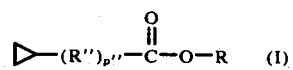  (I)

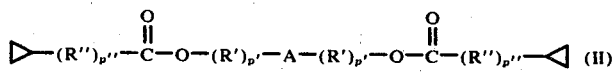  (II)

wherein,
R'' is the group —CH=CH— or the group —$(CH_2)_n$— in which $n$ is one, two, three or four;
p'' is zero or one;
R is alkyl of at least ten carbon atoms, alkenyl of at least ten carbon atoms, alkynyl of at least ten carbon atoms, cycloalkyl optionally substituted by one or more lower alkyl groups, or the group $$-CH-C=C-A'$$
$$\phantom{-CH-}\vert\phantom{C=}\vert\phantom{-}\vert$$
$$\phantom{-CH-}R^3\phantom{C=}R^4\phantom{-}R^5$$

in which each of $R^3$, $R^4$ and $R^5$ is hydrogen or lower alkyl and A' is phenyl, naphthyl, or cycloalkyl, each optionally substituted by one or more halogen, alkyl, alkoxy, aryl, aralkyl, aryloxy or aralkoxy groups;
R' is alkylene of one to six carbon atoms or alkenylene of two to six carbon atoms;
p' is zero or one; and
A is alkylene, alkenylene, alkynylene, cycloalkylene of four to six carbon atoms, optionally substituted by one or two alkyl or alkoxy groups; or arylene, optionally substituted by one or two groups selected from alkyl, halogen, or nitro.

Hereinafter each of n, P', p'', R, R', R'', $R^3$, $R^4$, $R^5$, A and A' is as defined above unless otherwise specified.

The compounds of formulas I and II are applied to the mite during the egg, larval or nymphal stages in view of their effect in causing inhibition of egg hatching, abnormal development leading to death, inability to pass from one stage to the next, or inability to reproduce. Some of the compounds also exhibit a residual ovicidal effect. A compound of formula I or II can be applied at concentration levels of the order of 0.001% to 1%, usually 0.01% to 0.1% by weight. Suitable carrier substances include liquid or solid inert carriers, such as water, acetone, xylene, mineral or vegetable oils, talc, vermiculite, and silica. Treatment of mites in accordance with the present invention can be accomplished by spraying, dusting, or otherwise contacting the mites and/or their eggs or larvae directly or indirectly. Generally, a concentration of less than 25% of active compound in the formulation is used depending on the type of application apparatus. The formulations can include emulsifying agents and wetting agents to assist in the application and effectiveness of the active ingredient.

The esters of Formula I and II can be prepared by reacting the appropriate mono- or di-hydric alcohol, i.e. ROH or HO-(R')$_p$ —A—(R')$_p$ —OH with at least one or two moles, respectively, of an acid of the formula

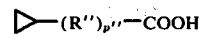

in the presence of an acid catalyst and with heating. The reaction can be carried out in the absence of a solvent; however, use of a solvent inert to the reaction, such as an ether or hydrocarbon solvent, is preferred. Water may be removed by azeotropic distillation, if desired.

Alternatively, the appropriate acid halide

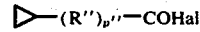

may be reacted with the corresponding mono- or di-hydric alcohol in the presence of pyridine and at either room temperature or, when the alcohol is sensitive to mineral acid, at from about −10° to about 0° C.

Acids of the formula

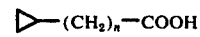

can be prepared from alkyl halides or sulfonates or from cyclopropanemethyl halides or sulfonates. Alkyl halides of the formula

can be prepared by reaction of an alcohol of the formula H$_2$C=CH—(CH$_2$)$_{n-1}$OH and CH$_2$I$_2$ in the presence of zinc-copper couple. The reaction is carried out in an inert solvent, such as an ether or hydrocarbon solvent, and proceeds satisfactorily with heating to yield

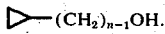

This alcohol intermediate is then converted to the halide with e.g. thionyl chloride in a solvent inert to the reaction and with cooling from −10° to 0° C. The reaction is carried out in the presence of a base such as pyridine or a trialkyl amine.

The alkyl chloride

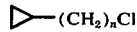

can be conveniently converted to the corresponding acid or acyl halide by reacting it with the anion of 1,3-dithiane, prepared with n-butyllithium in the presence of N,N,N',N'-tetramethylethylenediamine. The reaction is chilled to 0° to 10° for from seven to twenty-one days and the intermediate

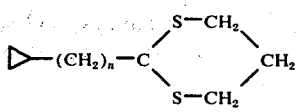

isolated. This intermediate is then treated with boron trifluoride, ether, red mercuric oxide and water in a solvent inert to the reaction to yield

The aldehyde can be oxidized to the acid using CrO$_3$ and sulfuric acid in the presence of acid and water.

The alkyl chlorides, except wherein n is one, can also be treated with magnesium metal and a Grignard initiator in an ether solvent inert to the reaction and then reacted with carbon dioxide to yield the corresponding acid.

The acids can also be prepared by a malonic ester synthesis wherein the halide of the formula

is treated with a malonic ester, for example, diethyl malonate, in the presence of sodium ethoxide and ethanol followed by the addition of sodium hydroxide and finally acidification and decarboxylation to yield the acid

Cyclopropanemethyl halides (n=1) can also be prepared by treating cyclopropanemethyl alcohol with an aromatic or aliphatic sulfonyl chloride, such as mesyl chloride or tosyl chloride, in pyridine solvent at 0°–10° C. The corresponding cyclopropanemethyl sulfonate thus formed is then treated with lithium bromide or lithium chloride in a solvent such as acetone to yield the corresponding cyclopropanemethyl chloride or bromide.

Cyclopropanemethyl chloride can also be prepared by treating cyclopropanemethyl alcohol with thionyl chloride according to the procedure described by Caserio et al., Tetrahedron II, 171 (1960).

The term "alkyl", as used herein, refers to a straight or branched chain saturated aliphatic hydrocarbon group of one to twenty-two carbon atoms, e.g., methyl, ethyl, propyl, i-propyl, n-butyl, s-butyl, t-butyl, pentyl, hexyl, heptyl, n-octyl, 2-methyloctyl, nonyl, decyl, undecyl, 2-methylundecyl, 6-methylundecyl, dodecyl, pentadecyl and the like. The term "lower alkyl" refers to an alkyl group of one to six carbon atoms.

The term "alkenyl" as used herein refers to a straight or branched chain unsaturated carbon chain containing ten to twenty-two carbon atoms and having one to three sites of olefinic unsaturation.

The term "alkynyl" as used herein refers to a straight or branched chain unsaturated carbon chain containing from ten to twenty-two carbon atoms and having one or two sites of acetylenic unsaturation.

The term "cycloalkyl", as used herein, refers to a monovalent cycloalkyl moiety of four to eight carbon atoms, i.e. cyclobutyl, cyclopentyl, cyclohexyl, cycloheptyl, and cyclooctyl.

The term "halogen", as used herein, refers to fluorine, chlorine and bromine.

The term "alkoxy", as used herein, refers to a straight or branched chain saturated aliphatic hydrocarbonoxy group of one to fifteen carbon atoms, e.g., methoxy, ethoxy, n-propoxy, i-propoxy, n-butoxy, i-butoxy, n-heptyloxy, n-dodecyloxy, 2-methyloctyloxy, and the like.

The term "aryl", as used herein, refers to a monovalent aromatic hydrocarbon group containing from six to fourteen carbon atoms such as phenyl, tolyl, xylyl, mesityl, naphthyl, ethylphenyl, t-butylphenyl, and isopropylphenyl.

The term "aralkyl", as used herein, refers to a monovalent hydrocarbon group containing from seven to fifteen carbon atoms in which a hydrogen atom of an alkyl group having a chain length of one to six carbon atoms is substituted by an aryl group, such as benzyl, phenethyl, methylbenzyl, napthylmethyl and naphthylethyl.

The term "aryloxy", as used herein, refers to an oxy-substituted aromatic hydrocarbon group of six to fourteen carbon atoms, such as, phenoxy, naphthyloxy, 4-ethylphenoxy, and the like.

The term "aralkoxy", as used herein, refers to an aromatic alkyloxy group of seven to fifteen carbon atoms, such as benzyloxy, 2-phenylethoxy, 4-methylbenzyloxy, naphthalenemethoxy, naphthyleneethoxy, and the like.

The term "alkylene", as used herein, refers to a bivalent radical derived from a normal or branched chain alkane containing one to twenty carbon atoms by removal of a hydrogen atom from each of two carbon atoms or two hydrogen atoms from one carbon atom.

The term "alkenylene" refers to a bivalent radical derived from a normal or branched chain alkene of two to twenty carbon atoms by removal of a hydrogen atom from each of two carbon atoms or two hydrogen atoms from one carbon atom.

The term "alkynylene" refers to the bivalent alkynylene moiety including branched chain alkynylene, of two to twenty carbon atoms.

The term "cycloalkylene", as used herein, refers to the bivalent cycloalkyl moiety of four to six carbon atoms, i.e. cyclobutylene, cyclopentylene and cyclohexylene.

The term "arylene" refers to any hydrocarbon group of six to twenty carbon atoms and containing at least one aromatic ring, e.g., phenylene or naphthylene, two phenyl or naphthyl rings joined by a single direct bond or by an atom of oxygen, sulfur, or nitrogen, indenylene, fluorenylene, dihydronaphthylene, tetrahydronaphthylene, anthracylene, phenanthrylene, and the like. The arylene group can be substituted by one or two groups selected from alkyl, halogen, or nitro.

With reference to the alkenyl, alkynyl, alkenylene and alkynylene groups defined above for A, R and R' in formulas I and II, for reasons of stability, the first carbon atom directly bonded to the oxygen of the ester group

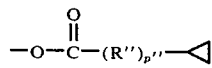

must be saturated. Thus, in the compounds of Formulas I and II, unsaturation of A, R and R' immediately adjacent to the oxygen atom of the ester group is excluded so that unstable enol esters do not fall within this invention.

The term "primary alkyl", "primary alkenyl", "primary alkynyl", "primary alkylene", "primary alkenylene", and "primary alkynylene" as used herein refer to those alkyl, alkenyl, alkynyl, alkylene, alkenylene and alkynylene groups, as defined above, wherein the carbon atom bonded directly to the oxygen atom of the ester function is further bonded to one carbon atom and two hydrogen atoms, i.e. a methylene radical ($-CH_2-$).

The esters of the present invention can be used alone or in an inert carrier substance for the control of mites (Acarina) or can be used in mixture with pesticides and/or juvenile hormone analogs known in the art in order to obtain a broader spectrum of activity. Suitable insecticides include Baygon, Captan, Sevin, Ciodrin, Systox, Diazinon, Vapona, Galecron, Cygon, Dimethrin, Dursban, Malathion, and Parathion. Typical juvenile hormone analogs which can be used in mixture with the compound of the present invention are described in U.S. Pat. Nos. 3,752,843 and 3,755,411.

The esters of the present invention are useful for the control of mites and ticks which are ectoparasitic on animals and birds. The compounds can be applied in either solution or in powder (dust) form in a conventional manner.

The following examples are provided to illustrate the sythesis of the esters of the present invention and the practice of the present invention. Temperature is in degrees Centigrade. All boiling points were measured by short path distillation.

For those compounds of formula I and II, e.g. the cyclohexane derivatives, where geometrical isomers can exist, each isomer and a mixture of isomers is included unless the isomeric configuration is specifically designated.

EXAMPLE 1

To a suspension of 40.0 g. of 3-buten-1-ol and 90.8 g. zinc-copper couple in 450 ml. of dry ether under nitrogen at room temperature is added about 15 ml. of diiodomethane. The reaction flask is heated externally with a heat gun until the reaction mixture refluxes by itself (about one hour). When the initial reflux rate begins to subside, 79 ml. of diiodomethane is added dropwise over a period of one-half hour to maintain a constant reflux rate. The reaction mixture is then heated to reflux by means of a water bath at 40°–45°, refluxed for five hours, allowed to sit overnight at room temperature and then refluxed for an additional six hours.

The reaction is quenched by first cooling the reaction mixture to room temperature and adding saturated ammonium chloride solution until gas evolution ceases and a black precipitate is formed. The reaction mixture is filtered and the solid filtrate washed twice with ether. The ether phase is then washed with a saturated aqueous solution of ammonium chloride, 3N sulfuric acid, 10% sodium bicarbonate, water and brine. The reaction mixture is then filtered, dried over calcium sulfate, filtered through activity III alumina, concentrated at atmospheric pressure, and distilled at reduced pressure to yield 25.8 g. of crude 2-cyclopropanethyl alcohol.

Using the procedure of this example, 3-cyclopropanepropyl alcohol and 4-cyclopropanebutyl alcohol are prepared from 4-penten-1-ol and 5-hexen-1-ol.

EXAMPLE 2

To a solution of 29.01 g. of 2-cyclopropaneethyl alcohol and 52.3 mls. tributyl amine (specific gravity = 0.778) in 200 mls. of anhydrous ether at 0° under nitrogen is added dropwise 15.8 mls. of thionyl chloride (specific gravity = 1.655). The reaction mixture is stored at -3° for four days and then poured into an ether/water mixture. The water phase is decanted away and the ether phase is washed with 5% soidum hydrogen carbonate, water, and brine and then dried over calcium sulfate, concentrated at atmospheric pressure and distilled at reduced pressure to yield 2-cyclopropaneethyl chloride.

Using the procedure of this example, cyclopropanemethyl chloride, 3-cyclopropanepropyl chloride and 4-cyclopropanebutyl chloride are prepared from cyclopropanemethyl alcohol, 3-cyclopropanepropyl alcohol and 4-cyclopropanebutyl alcohol respectively.

EXAMPLE 3

A mixture of 9.9 g. of 2-cyclopropaneethyl chloride, 150 mls. of anhydrous tetrahydrofuran, 2.41 g. of magnesium metal, and 0.87 g. of ethylene dibromide is heated to near boiling point for one hour. An additional 0.114 g. magnesium and 0.89 g. of ethylene bromide is then added and the reaction mixture is boiled for 4.25 hours at which time most of the magnesium metal has disappeared. Dry carbon dioxide gas is then continuously added over a period of one hour to the reaction mixture which is cooled with a water bath and stirred vigorously during this time. The reaction mixture is stirred overnight at 24° and then ether, water, and 3N sulfuric acid is added. The aqueous phase is separated and extracted twice with a one:one mixture of ether and pentane. The combined layers are washed with water and brine and then dried over calcium sulfate. The solvent is removed by rotary evaporation to yield 8.11 g. of 3-cyclopropanepropionic acid.

Using the procedure of this example, 4-cyclopropanebutyric acid and 5-cyclopropanevaleric acid are prepared from the corresponding chlorides prepared in Example 2.

EXAMPLE 4

To a mixture of 23.5 g. of 1,3-dithiane in 500 mls. of anhydrous tetrahydrofuran at -30° under nitrogen is added 133 mls. of 1.51 M n-butyllithium in hexane solution ever a period of one-half hour. The reaction mixture is stirred at −30° to −20° for two hours, warmed to −10°, and 23.5 g. of cyclopropanemethyl chloride and 15 mls. of N,N,N′,N′-tetramethylethylene 24 mls. of tetrahydrofuran is added. The reaction mixture is then refrigerated at 3° for fourteen days. Ether, pentane, and water are then added and the mixture is acidified with 100 mls. of aqueous 3N sulfuric acid. The aqueous layer is separated and extracted with a mixture of ether and pentane. The combined organic layers are then washed with water and brine, dried over calcium sulfate, and the solvent removed to yield 33.6 g. of a pale yellow product, 2-(cyclopropanemethyl)-1,3-dithiane.

To 230 mls. of aqueous tetrahydrofuran (15% water) is added 38.1 g. of boron trifluoride-ethyl ether, followed by 58 g. of red mercuric oxide. To this mixture is then added dropwise 23.4 g. of 2-(cyclopropanemethyl)-1,3-dithiane in 10 mls. of tetrahydrofuran. The mixture is stirred for five hours and then allowed to remain at 24° overnight. Ether (200 mls.) is added to the mixture and the upper phase decanted, washed twice with potassium carbonate, twice with brine and then dried over calcium sulfate. The mixture is filtered into a 15 cm. Vigreux distillation apparatus and the solvent removed to yield cyclopropaneacetaldehyde.

EXAMPLE 5

To a mixture of 0.10 g. of cyclopropaneacetaldehyde and 1 ml. of anhydrous acetone is added at 24° enough Jones Reagent (67 g. chromium trioxide, 125 mls. water, 58 mls. concentrated sulfuric acid, water to dissolve salts) to produce a persistent orange color. After five minutes, 50 mls. of ether and 10 mls. of water is added, the organic layer is separated and washed twice with 20 ml. portions of aqueous saturated sodium chloride solution and then dried over calcium sulfate. The solvent is removed by rotary evaporation to yield 0.12 g. of pale yellow liquid, 2-cyclopropaneacetic acid.

EXAMPLE 6

To a solution of 3.0 g. of 1,4-benzenedimethanol in 50 ml. of dry ether is added dropwise, under nitrogen, 11.35 g. of cyclopropanecarboxylic acid chloride. The reaction mixture is stirred for three days under nitrogen, poured into water and extracted with ether. The organic layer is washed with sodium bicarbonate, water and brine, dried over calcium sulfate, and the solvent evaporated to yield 1,4-dimethylenephenyl bis-(cyclopropanecarboxylate), 1,4-bis(cyclopropanecarbonyloxymethyl) benzene] having a melting point of 55°–57°. (II; $p''$ is zero, R' is methylene, $p'$ is one, A is 1,4-phenylene).

EXAMPLE 7

A mixture of 5.5 g. of 1,4-dihydroxybenzene, 15 g. of cyclopropane carboxylic acid chloride and 2.4 g. of magnesium in 55 ml. of dry benzene is refluxed for eight hours. The solution is then diluted with ether, washed with aqueous sodium bicarbonate, dilute aqueous hydrochloric acid, water and brine, dried over calcium sulfate, and recrystallized from ethanol/water to yield p-phenylene bis(cyclopropanecarboxylate), having a melting point of 137°. (II; $p'$ and $p''$ are zero, A is 1,4-phenylene).

Following the procedure of Example 7, cyclopropanecarboxylic acid chloride is reacted with 2,7-naphthalenediol, 2,5-naphthalenediol, 1,5-naphthalenediol, thiodiphenyl-4,4′-diol, biphenyl-4,4′-diol, and oxydiphenyl-4,4′-diol, 1,4-dihydroxy-2-methylbenzene, 2-chloro-1,4-dihydroxybenzene, 1,4-dihydroxy-2,5-dinitrobenzene, 1,4-dihidroxy-2-ethylbenzene, and 2-bromo-1,4-dihydroxybenzene to yield the respective ester:

2,7-naphthylene bis(cyclopropanecarboxylate), melting point 118.5°–120.5°;
2,5-naphthylene bis(cyclopropanecarboxylate), melting point 93°–4°;
1,5-naphthylene bis(cyclopropanecarboxylate), melting point 156°–8°;
4,4′-thiodiphenylene bis(cyclopropanecarboxylate);
4,4′-biphenylene bis(cyclopropanecarboxylate), melting point 147°–9°;
4,4′-oxydiphenylene bis(cyclopropanecarboxylate), melting point 100°–103°;
2-methyl-1,4-phenylene bis(cyclopropanecarboxylate);
2-chloro-1,4-phenylene bis(cyclopropanecarboxylate);
2,5-dinitro-1,4-phenylene bis(cyclopropanecarboxylate);
2-ethyl-1,4-phenylene bis(cyclopropanecarboxylate);
2-bromo-1,4-phenylene bis(cyclopropanecarboxylate);

EXAMPLE 8

To a stirred solution of 2.25 g. of cyclopropane carboxylic acid chloride in dry benzene, under nitrogen, is added 8 g. of 1-dodecanol. The mixture is stirred overnight and then diluted with pentane. The reaction mixture is worked up by washing with water and brine and then removing the solvent to yield dodecyl cyclopropanecarboxylate, b.p. 99°–100° (bath) at 0.03 mm. (I; $p''$ is zero, R is n-dodecyl).

By using an equivalent amount of each of 1-tetradecanol, 1-octadecanol, 1-hexadecanol, and 1-decanol in the process of this Example, there is prepared tetradecyl cyclopropanecarboxylate, b.p. 95.5° (bath) at 0.03 mm., octadecyl cyclopropanecarboxylate m.p. 32°, hexadecyl cyclopropanecarboxylate b.p. 154° bath at 0.05 mm., and decyl cyclopropanecarboxylate b.p. 85° (bath) at 0.1 mm.

Following the procedure of Example 8, cyclopropane carboxylic acid chloride is reacted with 1-tridecanol, 1-pentadecanol, 1-eicosanol, 2-tetradecanol, 2-methylhexadecan-1-ol, and 2,3-dimethylpentadecan-1-ol, to yield the following esters:

tridecyl cyclopropanecarboxylate, boiling point 87° at 0.2 mm;

pentadecyl cyclopropanecarboxylate, boiling point 100° at 0.05 mm;

eicosyl cyclopropanecarboxylate, melting point 40–41.5;

tetradec-2-yl cyclopropanecarboxylate, boiling point 112–114 at 0.04 mm;

2-methylhexadecyl cyclopropanecarboxylate, boiling point 150° at 0.02 mm; and 2,3-dimethylpentadecyl cyclopropanecarboxylate, boiling point 110° at 0.02 mm.

EXAMPLE 9

Following the procedure of Example 8, 9-octadecenyl cyclopropanecarboxylate, b.p. 159° (bath) at 0.05 mm. is prepared using 4.18 g. of cyclopropanecarboxylic acid chloride and 5.68 g. of 9-octadecen-1-ol in dry benzene.

Similarly, by reacting cyclopropanecarboxylic acid chloride and each of tetradeca-10,12-dien-1-ol, hexadeca-10,12,14-trien-1-ol, 13,17-dimethyloctadeca-10,12,16-trien-1-ol, octadeca-9,12-dien-1-ol, and octadeca-9,11,13-trien-1-ol following the procedure of Example 9, the following esters are obtained:

tetradeca-10,12-dien-1-yl cyclopropanecarboxylate
hexadeca-10,12,14-trien-1-yl cyclopropanecarboxylate
13,17-dimethyloctadeca-10,12,16-trien-1-yl cyclopropanecarboxylate
octadeca-9,12-dien-1-yl cyclopropanecarboxylate
octadeca-9,11,13-trien-1-yl cyclopropanecarboxylate

EXAMPLE 10

To a solution of 3.85 g. of 2-decyn-1-ol and 3.95 g. of pyridine in 100 ml. ether is added 3.0 g. of cyclopropanecarboxylic acid chloride. The mixture is stirred overnight under nitrogen. The reaction mixture is poured into distilled water, washed with dilute hydrochloric acid and then with sodium bicarbonate and solvent removed to yield 2-decynyl cyclopropanecarboxylate, b.p. 96°–97° (bath) at 0.1 mm.

Using the procedure of this Example, 3-decynyl cyclopropanecarboxylate, b.p. 78°–80° (bath) at 0.01 mm. is prepared from 3.0 g. of cyclopropanecarboxylic acid chloride and 3.85 g. of 3-decyn-1-ol.

Similarly, by reacting cyclopropanecarboxylic acid chloride and each of octadec-9-yn-1-ol, 7-methyltrideca-5,8-diyn-7-ol, tetradec-2-yn-1-ol, and hexadec-4-yn-1-ol following the procedure of this Example, the following esters are obtained:

octadec-9-yn-1-yl cyclopropanecarboxylate
7-methyltrideca-5,8-diyn-7-yl cyclopropanecarboxylate
tetradec-2-yn-1-yl cyclopropanecarboxylate
hexadec-4-yn-1-yl cyclopropanecarboxylate

EXAMPLE 11

To a mixture of 3.0 g. of 1,4-butynediol, 150 ml. of dry diethyl ether, and 16.9 ml. of dry pyridine at 0°, under argon, is added 10.9 g of cyclopropanecarboxylic acid chloride over a period of ten minutes. The mixture is stirred for two hours and then water and pentane are added. The mixture is washed with aqueous 3N sulfuric acid, aqueous potassium carbonate, water, aqueous saturated cupric sulfate, water, and brine, dried over calcium sulfate and the solvent removed to yield the bis-cyclopropanecarboxylate of 1,4-butynediol, [1,4-but-2-ynylene bis(cyclopropanecarboxylate)] b.p. 108°–111° (bath) at 0.05 mm.

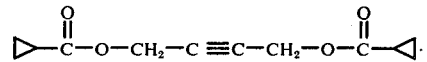

Following the procedure of this Example, 2 molar equivalents of cyclopropanecarboxylic acid chloride is reacted with 1 molar equivalent of hexa-2,4-diyn-1,6-diol to yield hexa-2,4-diyn-1,6-ylene bis(cyclopropanecarboxylate), boiling point 138°–140° at 0.04 mm.

Similarly, by reacting 2 molar equivalents of cyclopropane carboxylic acid chloride with each of hexa-2,4-dien-1,6-diol, but-1-ene-3,4-diol, 2,5-dimethylhex-3-yne-2,5-diol and hex-3-yne-2,5-diol, the following esters are obtained:

hexa-2,4-dien-1,6-ylene bis(cyclopropanecarboxylate)
but-1-en-3,4-ylene bis(cyclopropanecarboxylate)
dimethylhex-3-yn-2,5-ylene bis(cyclopropanecarboxylate)
hex-3-yn-2,5-ylene bis(cyclopropanecarboxylate)

EXAMPLE 12

Using the procedure of Example 11, each of 1,12-dodecanediol, 1,10-decanediol, 1,7-heptanediol, 1,6-hexanediol, 1,8-octanediol and 1,4-butanediol is reacted with cyclopropanecarboxylic acid chloride to yield the respective bis-ester.

bis-cyclopropanecarboxylate of 1,12-dodecanediol
[1,12-dodecamethylene bis(cyclopropanecarboxylate)]
bis-cyclopropanecarboxylate of 1,10-decanediol
1,10-decamethylene bis(cyclopropanecarboxylate)]
bis-cyclopropanecarboxylate of 1,7-heptanediol
[1,7-heptamethylene bis(cyclopropanecarboxylate)]
bis-cyclopropanecarboxylate of 1,6-hexanediol
1,6-hexamethylene bis(cyclopropanecarboxylate)]
bis-cyclopropanecarboxylate of 1,8-octanediol
[1,8-octamethylene bis(cyclopropanecarboxylate)]
bis-cyclopropanecarboxylate of 1,4-butanediol
[1,4-tetramethylene bis(cyclopropanecarboxylate)]

EXAMPLE 13

To a mixture of 1.14 g. of 3-cyclopropanepropionic acid, 30 mls. of anhydrous ether, and 1.1 mls. of thionyl chloride ($d_{10} = 1.66$), at 24°, was added 0.2 mls. of dimethyl formamide. The mixture is stirred for forty-five minutes and then the upper of the two layers that form is decanted away and excess thionyl chloride and solvent is removed from it by rotary evaporation to yield a pale orange liquid, 3-cyclopropanepropionyl chloride,

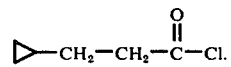

To the acid chloride, thus prepared, is added 40 mls. of anhydrous ether and 1.49 g. of 1-dodecanol, followed, at 0°, by 0.8 mls. of pyridine ($d_{20} = 0.982$). A white precipitate forms immediately. The mixture is stirred at 24° overnight and then water, ether, and pentane are added to the reaction mixture, the organic layer separated, washed with 3N sulfuric acid, aqueous 15% potassium carbonate, water, and brine, dried over calcium sulfate, and the solvent removed to yield dodecyl 3-cyclopropanepropionate, boiling point 116° at 0.05 mm.

By using an equivalent amount of 1-tetradecanol in the process of this example, there is prepared tetradecyl 3-cyclopropane propionate, boiling point 121°–123° at 0.03 mm.

Similarly, using an equivalent amount of 1-decanol, 1-tetradecanol, and 1-dodecanol with each of 4-cyclopropanebutyric acid and 5-cyclopropanevaleric acid in the procedure of this example, there is prepared:

decyl 4-cyclopropanebutyrate
tetradecyl 4-cyclopropanebutyrate
dodecyl 4-cyclopropanebutyrate
decyl 5-cyclopropanevalerate
tetradecyl 5-cyclopropanevalerate
dodecyl 5-cyclopropanevalerate Similarly, using an equivalent amount of 1-decanol, 1-pentadecanol, 1-hexadecanol, 1-octadecanol, hexadec-9-en-1-ol, octadec-6-en-1-ol, docos-13-en-1-ol, 3,7-dimethylocta-6-en-1-ol with 3-cyclopropanepropionyl chloride and 1-tridecanol and 3,7,11-trimethyldodeca-2,6,10-trien-1-ol with 4-cyclopropanebutyric acid, there is prepared:

decyl 3-cyclopropanepropionate
pentadecyl 3-cyclopropanepropionate
hexadecyl 3-cyclopropanepropionate
octadecyl 3-cyclopropanepropionate
hexadec-9-en-1-yl 3-cyclopropanepropionate
octadec-6-en-1-yl 3-cyclopropanepropionate
docos-13-en-1-yl 3-cyclopropanepropionate
3,7-dimethylocta-6-en-1-yl 3-cyclopropanepropionate
tridecyl 4-cyclopropanebutyrate
3,7,11-trimethyldodeca-2,6,10-trien-1-yl 4-cyclopropanebutyrate

EXAMPLE 14

To a mixture of 1.2 g. of cyclopropaneacetic acid, 30 mls. of anhydrous ether, and 1.3 mls. of thionyl chloride ($d_{10} = 1.66$), at 24°, is added 0.3 mls. of dimethylformamide. The mixture is stirred for 5½ hours, then the upper layer of the now two-phase mixture is decanted into another flask and all solvent and volatiles are removed by rotary evaporation. To the residue is added 40 mls. of dry ether and 2.19 g. of 1-pentadecanol in 20 mls. anhydrous ether, followed, at 0°, by 1 ml. of anhydrous pyridine ($d_{20} = 0.982$). The reaction mixture is allowed to warm to room temperature and stirred overnight. The product, pentadecyl cyclopropaneacetate, is isolated following the procedure of Example 13.

By using an equivalent amount of each of 1-dodecanol, 9-octadecen-1-ol, and 2-decyn-1-ol, respectively, and cyclopropane acetic acid in the process of this Example, there is prepared dodecyl cyclopropaneacetate, 9-octadecenyl cyclopropaneacetate, and 2-decynyl cyclopropaneacetate.

EXAMPLE 15

To a mixture of 3.0 g. of cyclopropanepropionic acid, 40 mls. of anhydrous ether, and 2.9 mls. of thionyl chloride ($d_{10} = 1.66$) at 24° is added 0.6 mls. of anhydrous dimethyl formamide. The mixture is stirred at 24° for three hours and the resultant upper layer decanted into another flask, the residue is washed with water and then combined with the decanted layer. The combined layers were concentrated by rotary evaporation to yield 3-cyclopropanepropionyl chloride.

To a mixture of 1.72 g. of the 3-cyclopropanepropionyl chloride (prepared above), 40 mls. of anhydrous ether, and 0.80 g. of benzene-1,4-dimethanol is added at 0°, under argon, 2.1 mls. of dry pyridine. The reaction mixture is allowed to warm to room temperature and then stirred overnight. The product 1,4-dimethylenephenyl bis(3-cyclopropylpropionoate or p-xylyene bis(3-cyclopropanepropionate) or 1,4-bis(cyclopropaneethylcarbonyloxymethyl)benzene, boiling point 155°–170° at 0.01 mm is isolated according to the procedure of Example 13.

By using an equivalent amount of 3-cyclopropanepropionic acid and each of 1,4-butynediol, 1,12-dodecanediol, 1,10-decanediol, 1,7-heptanediol, 1,6-hexanediol, 1,8-octanediol, 1,4-butanediol, 1,4-dihydroxycyclohexane, 1,4-dihydroxybenzene, and 2,5-dimethyl-1,4-dihydroxybenzene, but-2-ene-1,4-diol, hexa-1,5-dien-3,4-diol, hexa-2,4-diyne-1,6-diol, and octa-3,5-diyne-2,7-diol, in the process of this Example, there is prepared:

1,4-butynylene bis(3-cyclopropanepropionate)
1,12-dodecamethylene bis(3-cyclopropanepropionate)
1,10-decamethylene bis(3-cyclopropanepropionate)
1,7-heptamethylene bis(3-cyclopropanepropionate)
1,6-hexamethylene bis(3-cyclopropanepropionate)
1,8-octamethylene bis(cyclopropanepropionate)
1,4-tetramethylene bis(3-cyclopropanepropionate)
1,4-cyclohexylene bis(3-cyclopropanepropionate)
1,4-phenylene bis(3-cyclopropanepropionate)
2,5-dimethyl-1,4-phenylene bis(3-cyclopropanepropionate)
but-2-en-1,4-ylene bis(3-cyclopropanepropionate)
hexa-1,5-dien-3,4-ylene bis(3-cyclopropanepropionate)
hexa-2,4-diyn-1,6-ylene bis(3-cyclopropanepropionate)
octa-3,5-diyn-2,7-ylene bis(3-cyclopropanepropionate)

EXAMPLE 16

To a solution of 4.69 g. of cyclopropanecarboxylic acid chloride in 50 ml. ether at 0° under nitrogen is added 2.0 g. of 1,4-cyclohexanediol, followed by 4.17 ml. of pyridine (specific gravity = 0.98). The reaction mixture is allowed to warm to room temperature and then is stirred for six days. A mixture of ether and water is then added, the ether layer is separated, and the aqueous layer is extracted twice with ether. The combined organic phases are washed with 2 N sulfuric acid, 10% aqueous sodium carbonate, water, aqueous saturated copper sulfate, water and brine, dried over calcium sulfate, the solvent is removed and the residue is recrystallized from hexane to yield 2.58 g. of 1,4-cyclohexylene bis(cyclopropanecarboxylate), m.p. 113°–115°. The above compound can also be named as 1,4-bis(cyclopropylcarbonyloxy)cyclohexane)

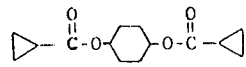

EXAMPLE 17

To a solution of 2.88 g. of 1,4-cyclohexanedimethanol in 100 ml. ether is added 5.3 g, of cyclopropanecarboxylic acid chloride. Upon the addition of 4.8 g. of pyridine, a precipitate forms immediately, accompanied by the evolution of a small amount of heat. The reaction mixture is stirred for one hour, water and pentane are added, the mixture is acidified with 3 N sulfuric acid, the organic phase is separated and then washed with water, potassium carbonate, saturated aqueous copper sulfate, water and brine. The solution is then dried and solvent removed to yield 1,4-dimethylenecyclohexane bis(cyclopropanecarboxylate). The above product can also be named as (1,4-bis(cyclopropylcarbonyloxymethyl)cyclohexane)

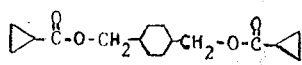

which is recrystallized from hexane.

Using the procedures similar to those of Examples 16 and 17, the compounds of Tables I–III are readily prepared.

TABLE I

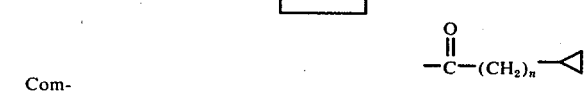

| Compound | n | R' | p' | X | Y |
|---|---|---|---|---|---|
| IA | zero | —(CH$_2$)$_2$— | one | H | H |
| IB | zero | —(CH$_2$)$_3$— | one | H | H |
| IC | zero | —CH$_2$—CH(CH$_3$)—CH$_2$— | one | H | H |
| ID | one | —CH$_2$— | one | H | H |
| IE | one | — | zero | H | H |
| IF | two | — | zero | H | H |
| IG | two | —CH$_2$— | one | H | H |
| IH | two | —(CH$_2$)$_2$— | one | H | H |
| IJ | two | —(CH$_2$)$_3$— | one | H | H |
| IK | two | —CH$_2$—CH(CH$_3$)—CH$_2$— | one | H | H |
| IL | three | — | zero | H | H |
| IM | three | —CH$_2$— | one | H | H |
| IN | four | —C(CH$_3$)$_2$— | one | H | H |
| IO | four | —H$_2$C—CH(CH$_3$)—CH$_2$— | one | H | H |
| IP | zero | — | zero | 2-CH$_3$ | 5-CH$_3$ |
| IQ | two | — | zero | 2-CH$_2$CH$_3$ | H |
| IR | zero | —CH$_2$— | one | 2-OCH$_3$ | H |
| IS | zero | — | zero | 2-CH(CH$_3$)$_2$ | H |
| IT | two | — | zero | 2-C(CH$_3$)$_3$ | H |
| IU | zero | CH$_2$ | one | 2-CH$_2$(CH$_2$)$_2$CH$_3$ | H |
| IV | zero | — | zero | 2-OCH$_3$ | 5-OCH$_3$ |
| IW | two | — | zero | 2-OCH$_2$CH$_3$ | 5-OCH$_2$CH$_3$ |
| IX | zero | CH$_2$ | one | 2-OCH$_2$CH$_3$ | H |

TABLE II

| Compound | n | R' | p' | X | Y |
|---|---|---|---|---|---|
| II A | zero | — | zero | H | H |
| II B | zero | —CH$_2$— | one | H | H |
| II C | one | — | zero | H | H |
| II D | two | — | zero | H | H |
| II E | two | —CH$_2$— | one | H | H |
| II F | three | —CH$_2$— | one | H | H |
| II G | four | —(CH$_2$)$_2$— | one | H | H |
| II H | zero | —(CH$_2$)$_2$— | one | 2-CH$_3$ | 4-CH$_3$ |
| II J | two | —(CH$_2$)$_2$— | one | H | 4-OCH$_2$CH$_3$ |
| II K | two | — | zero | H | 4-CH(CH$_3$)$_2$ |

TABLE III

| Compound | n | R' | p' | X | Y |
|---|---|---|---|---|---|
| III A | zero | — | zero | H | H |
| III B | zero | —CH$_2$— | one | H | H |
| III C | zero | —(CH$_2$)$_2$— | one | 2-CH$_3$ | H |
| III D | one | — | zero | 2-OCH$_3$ | H |
| III E | two | — | zero | H | H |
| III F | two | —CH$_2$— | one | H | H |
| III G | two | — | zero | 2-CH$_2$CH$_3$ | 4-CH$_2$CH$_3$ |
| III H | three | — | zero | H | H |
| III J | three | —CH$_2$— | one | H | H |
| III K | four | —(CH$_2$)$_2$— | one | H | H |

EXAMPLE 18 a. To a mixture of 8.00 g. of p-chlorocinnamic acid and 4.72 ml. of thionyl chloride in 50 ml. ether is added 1.01 ml. of dimethyl formamide. Two liquid phases are then formed and the reaction mixture is stirred overnight at room temperature. The upper phase is decanted and the solvent evaporated from it to yield p-chlorocinnamoyl chloride.

b. To a solution of p-chlorocinnamoyl chloride (prepared in a) above) in 80 ml. of tetrahydrofuran at −78° under nitrogen is added dropwise 10.35 ml. of a 2.54 M solution of lithium aluminum hydride in tetrahydrofuran. The reaction mixture is stirred for four hours at −78° and then is allowed to warm to room temperature overnight. Excess lithium aluminum hydride is quenched by successive addition of 1 ml. of water, 1 ml. of 15% sodium hydroxide and 3 ml. of water. The resultant mixture is filtered and the solid washed several times with ether. The ether-tetrahydrofuran solution is washed with water, 0.1 N sodium hydroxide, aqueous sodium and potassium tartarate, water and brine. The solution is then dried over calcium sulfate and concentrated to give 6.74 g. of p-chlorocinnamyl alcohol.

Using the procedure of Example 18, the alcohols of Column II are prepared from the acids of Column I.

I cinnamic acid
p-methoxycinnamic acid
p-benzylcinnamic acid
p-benzyloxycinnamic acid
4-(benzyloxy)-3,5-dimethoxycinnamic acid
m-bromocinnamic acid
p-bromocinnamic acid
p-n-butoxycinnamic acid
4-n-butoxy-3-fluorocinnamic acid
p-chlorocinnamic acid
3-chloro-4-methoxycinnamic acid
2-chloro-5-methylcinnamic acid
p-(n-dodecyloxy)cinnamic acid
p-ethoxycinnamic acid
p-ethylcinnamic acid
m-fluorocinnamic acid
p-(isohexyloxy)cinnamic acid
p-isopropoxycinnamic acid
p-methylcinnamic acid
p-isopropylcinnamic acid
o-methoxycinnamic acid
p-(p-methylphenethyl)cinnamic acid
p-(n-octyloxy)cinnamic acid
p-phenoxycinnamic acid
p-phenylcinnamic acid
2,4,5-trimethoxycinnamic acid

II cinnamyl alcohol
p-methoxycinnamyl alcohol
p-benzylcinnamyl alcohol
p-benzyloxycinnamyl alcohol
4-(benzyloxy)-3,5-dimethoxycinnamyl alcohol
m-bromocinnamyl alcohol
p-bromocinnamyl alcohol
p-n-butoxycinnamyl alcohol
4-n-butoxy-3-fluorocinnamyl alcohol
p-chlorocinnamyl alcohol
3-chloro-4-methoxycinnamyl alcohol
2-chloro-5-methylcinnamyl alcohol
p-(n-dodecyloxy)cinnamyl alcohol
p-ethoxycinnamyl alcohol
p-ethylcinnamyl alcohol
m-fluorocinnamyl alcohol
p-(isohexyloxy)cinnamyl alcohol
p-isopropoxycinnamyl alcohol
p-methylcinnamyl alcohol
p-isopropylcinnamyl alcohol
o-methoxycinnamyl alcohol
p-(p-methylphenethyl)cinnamyl alcohol
p-(n-octyloxy)cinnamyl alcohol
p-phenoxycinnamyl alcohol
p-phenylcinnamyl alcohol
2,4,5-trimethoxycinnamyl alcohol

EXAMPLE 19

To a solution of 2.5 g. of p-chlorocinnamyl alcohol in 50 ml. ether at 0° under nitrogen is added 2.33 g. of cyclopropanecarbonyl chloride and 3.6 ml. of pyridine. The reaction mixture is allowed to warm to room temperature and is then stirred for ten days. Water is then added to dissolve the pyridinium hydrochloride and form a second liquid phase. This mixture is stirred for four hours to hydrolyze the excess acid chloride and the mixture is then diluted with a mixture of ether and water. The ether phase is separated and the aqueous phase is extracted once with ether. The combined ether phases are washed with 2N sulfuric acid, 10% potassium carbonate, water, saturated copper sulfate, water, and brine, dried over calcium sulfate, and the solvent removed to yield 2.35 g. of p-chlorocinnamyl cyclopropanecarboxylate, boiling point 125° at 0.15 mm.

Following the procedure of Example 19, the esters of Column III are prepared from the alcohols of Column II.

III cinnamyl cyclopropanecarboxylate
p-methoxycinnamyl cyclopropanecarboxylate
p-benzylcinnamyl cyclopropanecarboxylate
p-benzyloxycinnamyl cyclopropanecarboxylate
4-(benzyloxy)-3,5-dimethoxycinnamyl cyclopropanecarboxylate
m-bromocinnamyl cyclopropanecarboxylate
p-bromocinnamyl cyclopropanecarboxylate
p-(n-butoxy)cinnamyl cyclopropanecarboxylate
4-(n-butoxy)-3-fluorocinnamyl cyclopropanecarboxylate
p-chlorocinnamyl cyclopropanecarboxylate
3-chloro-4-methoxycinnamyl cyclopropanecarboxylate
2-chloro-5-methylcinnamyl cyclopropanecarboxylate
p-(n-dodecyloxy)cinnamyl cyclopropanecarboxylate
p-ethoxycinnamyl cyclopropanecarboxylate
p-ethylcinnamyl cyclopropanecarboxylate
m-fluorocinnamyl cyclopropanecarboxylate
p-(isohexyloxy)cinnamyl cyclopropanecarboxylate
p-isopropoxycinnamyl cyclopropanecarboxylate
p-methylcinnamyl cyclopropanecarboxylate
p-isopropylcinnamyl cyclopropanecarboxylate
o-methoxycinnamyl cyclopropanecarboxylate
p-(p-methylphenethyl)cinnamyl cyclopropanecarboxylate
p-(n-octyloxy)cinnamyl cyclopropanecarboxylate
p-phenoxycinnamyl cyclopropanecarboxylate
p-phenylcinnamyl cyclopropanecarboxylate
2,4,5-trimethoxycinnamyl cyclopropanecarboxylate

EXAMPLE 20

To a solution of 0.10 g. of 3-cyclopropanepropionic acid and 0.85 ml. of thionyl chloride in 10 ml. of ether is added 0.2 ml. of dimethyl formamide. The reaction mixture is stirred overnight at room temperature and then an additional 0.3 ml. of thionyl chloride is added and the reaction stirred for three hours. The upper layer of the resultant two-phase mixture is decanted and the solvent removed from it to yield 3-cyclopropanepropionyl chloride.

To a solution of this 3-cyclopropanepropionyl chloride and 0.99 g. of p-methylcinnamyl alcohol in 25 ml. of ether under nitrogen at 0° is added 1.0 ml. of pyridine. The reaction mixture is allowed to warm to room temperature and then is stirred for four days. Ether is added to the reaction mixture, the organic phase separated and the aqueous phase extracted with ether. The combined organic phases are worked up as in Example 19 to yield 1.05 g. of p-methylcinnamyl 3-cyclopropanepropionate, which is purified by preparative thin layer chromatography and by short path distillation at 120° (bath) at 0.2 mm.

Using the procedure of this Example, the esters of Column IV are prepared using the alcohols of Column II and the acid chlorides of the acids of Examples 3 and 5.

IV cinnamyl 3-cyclopropanepropionate
p-methoxycinnamyl 3-cyclopropanepropionate
p-benzylcinnamyl 5-cyclopropanepentanoate
p-benzyloxycinnamyl 3-cyclopropanepropionate
4-(benzyloxy)-3,5-dimethoxycinnamyl 2-cyclopropaneacetate
m-bromocinnamyl 4-cyclopropanebutyrate
p-bromocinnamyl 5-cyclopropanepentanoate
p-butoxycinnamyl 3-cyclopropanepropionate
4-butoxy-3-fluorocinnamyl 2-cyclopropaneacetate
p-chlorocinnamyl 3-cyclopropanepropionate
3-chloro-4-methoxycinnamyl 3-cyclopropanepropionate
2-chloro-5-methylcinnamyl 2-cyclopropaneacetate
p-(dodecyloxy)cinnamyl 3-cyclopropanepropionate
p-ethoxycinnamyl 3-cyclopropanepropionate
p-ethylcinnamyl 3-cyclopropanepropionate
m-fluorocinnamyl 3-cyclopropanepropionate
p-(isohexyloxy)cinnamyl 3-cyclopropanepropionate
p-isopropoxycinnamyl 3-cyclopropanepropionate
p-isopropylcinnamyl 3-cyclopropanepropionate
p-methylcinnamyl 3-cyclopropanepropionate
o-methoxycinnamyl 3-cyclopropanepropionate
p-(p-methylphenethyl)cinnamyl 3-cyclopropanepropionate
p-(n-octyloxy)cinnamyl 3-cyclopropanepropionate
p-phenoxycinnamyl 3-cyclopropanepropionate
p-phenylcinnamyl 3-cyclopropanepropionate
2,4,5-trimethoxycinnamyl 4-cyclopropanebutyrate The alcohols where each of $R^3$, $R^4$, and $R^5$ is hydrogen or where $R^5$ is alkyl and $R^3$ and $R^4$ are hydrogen can be prepared by treating a carbonyl compound of the formula $A'—C(O)—R^5$ with an equimolar amount of triethyl phosphonoacetate in dimethyl formamide solution containing a slight molar excess of sodium hydroxide or sodium hydride. The reaction is carried out under nitrogen and at from 20° to reflux. The resultant ethyl ester is then reduced with diisobutylaluminum hydride to the desired alcohol.

The alcohols where $R^3$ and $R^5$ are hydrogen and $R^4$ is alkyl can be prepared by treating an aldehyde of the formula $A'—C(O)H$ with a compound of the formula

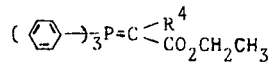

in an inert solvent from 20° to reflux followed by reduction, as above, to the alcohol.

The alcohols where $R^4$ and $R^5$ are hydrogen and $R^3$ is alkyl are prepared by treating an aldehyde

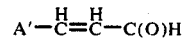

with a Grignard reagent $R^3MgCl$ using a procedure as described in Organic Syntheses, Collective Vol. 3, page 696 to obtain the desired alcohol.

Using the above procedures, the alcohols of Column V are prepared.

V 3-cyclohexyl-2-propen-1-ol
3-cyclobutyl-2-propen-1-ol
3-cyclopentyl-2-propen-1-ol
3-cycloheptyl-2-propen-1-ol
3-cyclooctyl-2-propen-1-ol
3-(4-methoxycyclohexyl)-2-propen-1-ol
3-(4-chlorocyclohexyl)-2-propen-1-ol
3-(4-n-octylcyclohexyl)-2-propen-1-ol
3-(4-methylcyclohexyl)-2-propen-1-ol
3-(1-naphthyl)-2-propen-1-ol
3-(2-naphthyl)-2-propen-1-ol
3-(4-chloronaphth-1-yl)-2-propen-1-ol
3-(6-methoxynaphth-2-yl)-2-propen-1-ol
3-(4-methylnaphth-1-yl)-2-propen-1-ol
3-(4-n-octylnaphth-1-yl)-2-propen-1-ol
3-cyclohexyl-3-methyl-2-propen-1-ol
3-cyclohexyl-3-isopropyl-2-propen-1-ol
3-(1-naphthyl)-3-ethyl-2-propen-1-ol
3-(2-naphthyl)-2-methyl-2-propen-1-ol
3-(4-chlorophenyl)-3-methyl-2-propen-1-ol
3-(4-methylphenyl)-3-methyl-2-propen-1-ol
3-(4-chlorophenyl)-2-ethyl-2-propen-1-ol
3-(4-methylphenyl)-2-butyl-2-propen-1-ol
3-(4-methoxyphenyl)-1-methyl-2-propen-1-ol
3-(4-n-octylphenyl-1-ethyl-2-propen-1-ol Following the procedure of Example 20, the esters of Column VI are prepared using the alcohols of Column V and the acid chlorides of the acids of Examples 3 and 5.

VI 3-cyclohexyl-2-propen-1-yl 3-cyclopropanepropionate
3-cyclobutyl-2-propen-1-yl 3-cyclopropanepropionate
3-cyclopentyl-2-propen-1-yl 5-cyclopropanepentanoate
3-cycloheptyl-2-propen-1-yl 3-cyclopropanepropionate
3-cyclooctyl-2-propen-1-yl 2-cyclopropaneacetate
3-(4-methoxycyclohexyl)2-propen-1-yl 4-cyclopropanebutyrate
3-(4-chlorocyclohexyl)-2-propen-1-yl 5-cyclopropanepentanoate
3-(4-n-octylcyclohexyl)-2-propen-1-yl 2-cyclopropaneacetate
3-(4-methylcyclohexyl)-2-propen-1-yl 3-cyclopropanepropionate
3-(1-naphthyl)-2-propen-1-yl 3-cyclopropanepropionate
3-(2-naphthyl)-2-propen-1-yl 3-cyclopropanepropionate 3-(4-chloronaphth-1-yl)-2-propen-1-yl 3-cyclopropanepropionate
3-(6-methoxynaphth-2-y)-2-propen-1-yl 3-cyclopropanepropionate
3-(4-methynaphth-1-yl)-2-propen-1-yl 3-cyclopropanepropionate
3-(4-n-octylnaphth-1-yl)-2-propen-1-yl 3-cyclopropanepropionate
3-cyclohexyl-3-methyl-2-propen-1-yl 3-cyclopropanepropionate
3-cyclohexyl-3-isopropyl-2-propen-1-yl 3-cyclopropanepropionate
3-(1-naphthyl)-3-ethyl-2-propen-1-yl 3-cyclopropanepropionate
3-(2-naphthyl)-2-methyl-2-propen-1-yl 3-cyclopropanepropionate
3-(4-chlorophenyl)-3-methyl-2-propen-1-yl 3-cyclopropanepropionate
3-(4-methylphenyl)-3-methyl-2-propen-1-yl 3-cycloypropanepropionate
3-(4-chlorophenyl)-2-ethyl-2-propen-1-yl 3cyclopropanepropionate
3-(4-methylphenyl)-2-butyl-2-propen-1-yl 3-cyclopropanepropionate
3-(4-methoxyphenyl)-1-methyl-2-propen-1-yl 3-cyclopropanepropionate
3-(4-n-octylphenyl)-1-ethyl-2-propen-1-yl 3-cyclopropanepropionate

EXAMPLE 21

To a mixture of 700 ml. of anhydrous methylene chloride, 32.2 ml. of anhydrous pyridine and 50 g. of barium oxide at room temperature under nitrogen is added 22.0 g. of chromium trioxide. The mixture is stirred at room temperature for three hours and then 7.21 g. of cyclopropanemethyl alcohol in 10 ml. of methylene chloride is added, with stirring, over a 10 minute period. The mixture is stirred for 1.5 hours and then is poured directly onto 120 g. of Florisil (chromatographic magnesium silicate). The column is drained and washed with 100 ml. of methylene chloride. The eluate is dried over calcium sulfate, filtered, and purified by distillation to yield cyclopropanecarbaldehyde.

EXAMPLE 22

To a mixture of 2.34 g. of cyclopropanecarbaldehyde in pyridine, 19 ml. anhydrous dimethylformamide and 7.47 g. of triethylphosphonoacetate at room temperature under argon is added 1.47 g. of sodium hydroxide. The mixture is surrounded by a room temperature water bath and is stirred overnight. Ether (50 ml.), pentane (50 ml.), and water (100 ml.) are then added and the mixture is acidified with aqueous 3N sulfuric acid to a pH of 2. The aqueous layer is separated and extracted twice with 40 ml. portions of aqueous saturated sodium chloride solution and then dried over copper sulfate. The mixture is filtered and then is distilled to yield 2.84 g. ethyl 3-cyclopropaneprop-2-enoate.

EXAMPLE 23

A mixture of 2.0 g. of ethyl 3-cyclopropaneprop-2-enoate, 8 ml. of methanol, 4 ml. of water, and 0.74 g. of sodium hydroxide is boiled for two hours. Ether (7 ml.), pentane (25 ml.), water (100 ml.) and aqueous saturated sodium chloride (100 ml.) are added to the mixture which is then acidified with aqueous 3N sulfuric acid (10 ml.). The aqueous layer is separated and is extracted twice with 50 ml. portions of a 2:1 mixture of ether and pentane. The combined organic layers are washed twice with 40 ml. portions of aqueous saturated sodium chloride solution and then are dried over calcium sulfate. The solvent is removed by evaporation to yield 1.11 g. of 3-cyclopropaneprop-2-enoic acid.

EXAMPLE 24

To a mixture of 0.9 g. of 3-cyclopropaneprop-2-enoic acid, 30 ml. of anhydrous ether, and 0.9 ml. of thionyl chloride at room temperature is added 0.2 ml. of anhydrous dimethyl formamide. The mixture is stirred for six hours at room temperature at which time the upper layer of the biphasic mixture is decanted away and the volatile material removed from it by roto evaporation.

The residue remaining after evaporation is taken up in 50 ml. anhydrous ether and to it is added 1.37 g. of 1-tetradecanol followed, at 0°, by 0.6 ml. of pyridine. The reaction mixture is allowed to warm to room temperature and is stirred at room temperature for four days. The reaction mixture is worked up using the procedure of Example 13 to yield 1.3 ml. of tetradecyl 3-cyclopropaneprop-2-enoate.

Following the procedure of this Example, 3-cyclopropaneprop-2-enoic acid is reacted with each of 1-decanol, 1-dodecanol, 1-hexadecanol, 1-octadecanol, 9-octadecen-1-ol, 3-decyn-1-ol, 1-pentadecanol, 1-tridecanol, 1-eicosanol, 2-tetradecanol, 2-methylhexadecan-1-ol, 2-methyltetradecan-1-ol, and 2,3-dimethylpentadecan-1-ol in approximately equimolar ratios and 3-cyclopropaneprop-2-enoic acid is reacted with each of 1,4-benzenedimethanol, but-2-yn-1,4-diol, 1,4-dihydroxybenzene, 1,12-dodecanediol, 1,10-decanediol, 1,4-cyclohexanedimethanol, 2,7-naphthalenediol, 1,4-cyclohexanediol, 2,4-hexadiyn-1,6-diol, 2,5-naphthalenediol, 4,4'-thiodibenzenediol, 1,4-naphthalendiol, 4,4'-thiodibenzenediol, 1,4-naphthalenediol, 4,4'-dibenzenediol, and 4,4'-oxydibenzenediol in the approximate molar ratio of 2 equivalents acid to one equivalent diol to yield the following esters:

decyl 3-cyclopropaneprop-2-enoate
dodecyl 3-cyclopropaneprop-2-enoate
hexadecyl 3-cyclopropaneprop-2-enoate
octadecyl 3-cyclopropaneprop-2-enoate
9-octadecenyl 3-cyclopropaneprop-2-enoate
3-decynyl 3-cyclopropaneprop-2-enoate
pentadecyl 3-cyclopropaneprop-2-enoate
tridecyl 3-cyclopropaneprop-2-enoate
eicosyl 3-cyclopropaneprop-2-enoate
2-tetradecyl 3-cyclopropaneprop-2-enoate
2-methylhexadecyl 3-cyclopropaneprop-2-enoate
2-methyltetradecyl 3-cyclopropaneprop-2-enoate
2,3-dimethylpentadecyl 3-cyclopropaneprop-2-enoate
1,4-xylylene bis(3-cyclopropaneprop-2-enoate)
1,4-but-2-ynylene bis(3-cyclopropaneprop-2-enoate)
1,4-phenylene bis(3-cyclopropaneprop-2-enoate)
1,12-dodecamethylene bis(3-cyclopropaneprop-2-enoate)
1,10-decamethylene bis(3-cyclopropaneprop-2-enoate)
1,4-cyclohexanedimethylene bis(3-cyclopropaneprop-2-enoate)
2,7-naphthylene bis(3-cyclopropaneprop-2-enoate)
1,4-cyclohexylene bis(3-cyclopropaneprop-2-enoate)

hexa-2,4-diyn-1,6-ylene bis(3-cyclopropaneprop-2-enoate)
2,5-naphthylene bis(3-cyclopropaneprop-2-enoate)
4,4'-thiodiphenylene bis(3-cyclopropaneprop-2-enoate)
1,4-naphthylene bis(3-cyclopropaneprop-2-enoate)
4,4'-biphenylene bis(3-cyclopropaneprop-2-enoate)
4,4'-oxydiphenylene bis(3-cyclopropaneprop-2-enoate)

A wettable powder suitable for field application after dilution can be formulated by blending and then airmilling a mixture of 20 to 30% of an ester of this invention, 60 to 70% of a solid carrier such as Attaclay X-250, 1 to 3% of an anionic surfactant, such as Igepon T-77, and 3 to 5% of a dispersing agent such as Marasperse N-22.

A typical formulation is as follows:

| | |
|---|---|
| Active ingredient[1] | 25.0% |
| Synthetic calcium silicate | 40.0% |
| Attapulgite Clay | 29.0% |
| Sodium lignosulfonate | 4.0% |
| Sodium N-methyl N-olcoyl taurate | 2.0% |

[1]The active ingredient is selected from one or more of the following:
  hexadecyl cyclopropanecarboxylate
  octadecyl cyclopropanecarboxylate
  tetradecyl 3-cyclopropanepropionate
  tetradecyl 3-cyclopropaneprop-2-enoate
  1,10-decamethylene bis(cyclopropanecarboxylate)
  1,4-dimethylenecyclohexane bis(cyclopropanecarboxylate)
  1,4-phenylene bis(cyclopropanecarboxylate)
  p-methylcinnamyl 3-cyclopropanepropionate
  1,4-bis(cyclopropanecarbonyloxymethyl)benzene The wettable powder is applied, after dilution with water, using ultra-low volume sprayers. Dilutions containing the ester within a concentration range of about 0.01% to 10% are generally employed.

The compound p-chlorocinnamyl cyclopropanecarboxylate can be formulated as a 25% active ingredient dust having the following composition:

| | |
|---|---|
| p-chlorocinnamyl cyclopropanecarboxylate | 25% |
| Synthetic Calcium Silicate | 5% |
| Attapulgite Clay | 68.5% |
| Dust Inhibitor and Sticker | 1.5% |

The compound p-methylcinnamyl 3-cyclopropanepropionate is formulated as an emulsifiable concentrate having the following composition:

| | |
|---|---|
| p-methylcinnamyl 3-cyclopropanepropionate | 57.5% |
| Xylene | 34.5% |
| Mixture of nonionic and anionic surfactants | 8.0% |

The mite control agents of the present invention can be used alone in an inert agriculturally acceptable carrier substance for the control of mites (Arachnids) or can be used in mixture with insecticides and/or juvenile hormone analogs known in the art to provide a broader spectrum of activity on more developmental stages of the mites or on other pestiferous insect species.

The effectiveness of the compounds of the present invention is demonstrated below.

Adults (*Tetranychus urticae*) are allowed to oviposit for twenty-four hours on castor bean leaf discs (diameter 1 cm.) on moist cottonwool.

After twenty-four hours, the adults are removed and the leaf discs are then dipped in acetone solutions of the compound being tested.

After submersion for one second, the solvent on the leaf discs is allowed to dry and the leaf discs are then glued to a plastic petri dish to prevent crumpling.

Six days later (when all the eggs on untreated discs have emerged), the number of unhatched eggs is calculated as a percentage of the total number originally present, corrected for any spontaneous non-emergence observed in control discs treated only with solvent (Abbott correction).

Table IV presents the results of biological testing conducted as outlined above.

TABLE IV

| Compound | % concentration in solution | % hatching prevented |
|---|---|---|
| 1,4-bis(cyclopropanecarbonyloxymethyl)benzene | 0.1 | 100 |
| hexadecyl cyclopropanecarboxylate | 0.1 | 100 |
| tetradecyl 3-cyclopropanepropionate | 0.01 | 100 |
| 1,4-cyclohexylene bis(cyclopropanecarboxylate) | 0.1 | 100 |
| p-chlorocinnamyl cyclopropanecarboxylate | 0.1 | 100 |
| p-methylcinnamyl 3-cyclopropanepropionate | 0.1 | 100 |
| octadec-9-en-1-yl cyclopropanecarboxylate | 0.1 | 100 |
| dec-3-yn-1-yl cyclopropanecarboxylate | 0.1 | 100 |
| 1,4-but-2-ynylene bis(cyclopropanecarboxylate) | 0.1 | 100 |
| tetradecyl 3-cyclopropane-2-propenoate | 0.1 | 100 |
| 1,4-but-2-ynylene bis(3-cyclopropanepropionate) | 0.1 | 100 |
| 1,4-phenylene bis(3-cyclopropanecarboxylate) | 0.1 | 100 |

What is claimed is:
1. A method for the control of mites of the order Acarina which comprises contacting the acarid at the egg or larval stage with an ovicidally effective amount or larvicidally effective amount of a compound of the formula (I) or (II):

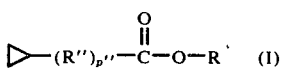

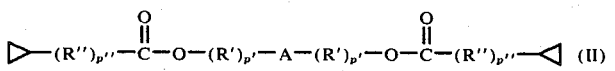

wherein,
R'' is —CH=CH— or —(CH$_2$)$_n$— in which $n$ is a positive number from one to four;
$p''$ is zero or one;
R is alkyl of ten to twenty-two carbon atoms, alkenyl of ten to twenty-two carbon atoms and having one to three sites of olefinic unsaturation, alkynyl of ten to twenty-two carbon atoms and having one or two sites of acetylenic unsaturation or the group

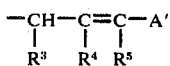

in which A' is phenyl, naphthyl or cycloalkyl of four to eight carbon atoms, each ring being optionally substituted by one or more halogen, alkyl of one to twenty-two carbon atoms, alkoxy of one to fifteen carbon atoms, aryl of six to fourteen carbon atoms, aralkyl of seven to fifteen carbon atoms, aryloxy of six to fourteen carbon atoms or aralkoxy of seven to fifteen carbon atoms groups, and each of $R^3$, $R^4$ and $R^5$ is hydrogen or lower alkyl;

p' is zero or one;

R' is alkylene of one to six carbon atoms or alkenylene of two to six carbon atoms; and A is alkylene of two to twenty carbon atoms, alkenylene of two to twenty carbon atoms and having one to three sites of olefinic unsaturation, alkynylene of two to twenty carbon atoms and having one or two sites of acetylenic unsaturation, arylene of six to twenty carbon atoms optionally substituted by one or two groups selected from alkyl of one to twenty-two carbon atoms, halogen or nitro, or cycloalkylene of four to six carbon atoms optionally substituted by one or two alkyl groups of one to twenty-two carbon atoms or one or two alkoxy groups of one to fifteen carbon atoms.

2. The method of claim 1 wherein said compound is a compound of formula I wherein p'' is zero and R is primary alkyl, primary alkenyl or primary alkynyl.

3. The method of claim 2 wherein R is a primary unbranched alkyl of thirteen to twenty carbon atoms.

4. The method of claim 3 wherein the acarid is a mite of the family Tetranychidae or the family Tarsonemidae.

5. The method of claim 3 wherein the acarid is a mite of the genus Tetranychus, the genus Bryobia, the genus Oligonychus or the genus Panonychus.

6. The method of claim 3 wherein the compound is

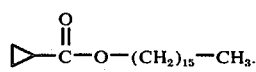

7. The method of claim 3 wherein the compound is

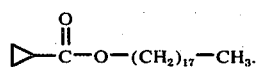

8. The method of claim 6 wherein the acarid is a mite of the genus Tetranychus.

9. The method of claim 7 wherein the acarid is a mite of the genus Tetranychus.

10. The method of claim 1 wherein said compound is a compound of the formula:

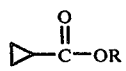

in which R is a primary unbranched alkenyl of twelve to eighteen carbon atoms and the acarid is a mite of the family Tetranychidae or the family Tarsonemidae.

11. The method of claim 10 wherein said compound is 9-octadecenyl cyclopropanecarboxylate and the acarid is a mite of the genus Tetranychus, the genus Bryobia, the genus Oligonychus or the genus Panonychus.

12. The method of claim 1 wherein said compound is a compound of the formula:

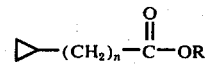

wherein R is primary alkyl, primary alkenyl or primary alkynyl and the acarid is a mite of the family Tetranychidae or the family Tarsonemidae.

13. The method of claim 12 wherein n is two or four, R is primary unbranched alkyl of ten to eighteen carbon atoms and the acarid is a mite of the genus Tetranychus, the genus Bryobia, the genus Oligonychus or the genus Panonychus.

14. The method of claim 13 wherein the compound is hexadecyl 3-cyclopropanepropionate.

15. The method of claim 13 wherein the compound is decyl 3-cyclopropanepropionate.

16. The method of claim 13 wherein the compound is dodecyl 3-cyclopropanepropionate.

17. The method of claim 1 wherein said compound is

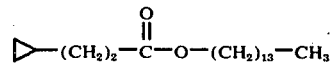

and the acarid is a mite of the genus Tetranychus.

18. The method of claim 13 wherein said compound is a compound of the formula

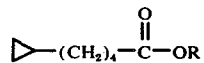

wherein R is decyl, dodecyl, tetradecyl or hexadecyl.

19. The method of claim 1 wherein said compound is a compound of the formula:

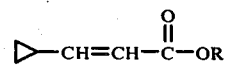

wherein R is primary alkyl of ten to eighteen carbon atoms and the acarid is a mite of the family Tetranychidae or the family Tarsonemidae.

20. The method of claim 19 wherein R is dodecyl, tetradecyl, hexadecyl or octadecyl.

21. The method of claim 19 wherein said compound is

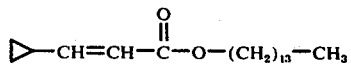

and the acarid is a mite of the genus Tetranychus.

22. The method according to claim 1 wherein the compound is

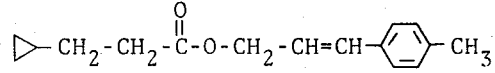

and the acarid is a mite of the genus Tetranychus, the genus Bryobia, the genus Oligonychus or the genus Panonychus.

23. The method according to claim 1 wherein said compound is a compound of the formula:

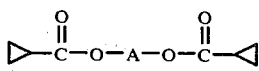

wherein A is alkylene of two to twenty carbon atoms, alkenylene of two to twenty carbon atoms or alkynylene of two to twenty carbon atoms and the acarid is a mite of the family Tetranychidae or the family Tarsonemidae.

24. The method according to claim 23 wherein in said formula, A is primary alkylene of eight to sixteen carbon atoms.

25. The method of claim 24 wherein A is decamethylene and the acarid is a mite of the genus Tetranychus, the genus Bryobia, the genus Oligonychus or the genus Panonychus.

26. The method of claim 24 wherein A is dodecamethylene and the acarid is a mite of the genus Tetranychus, the genus Bryobia, the genus Oligonychus or the genus Panoychus.

27. The method according to claim 23 wherein in said formula, A is primary alkynylene of four to ten carbon atoms.

28. The method according to claim 23 wherein said compound is

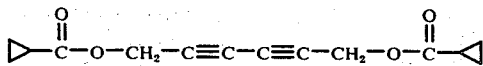

and the acarid is a mite of the genus Tetranychus.

29. The method according to claim 1 wherein said compound is a compound of the formula:

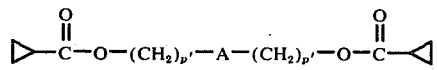

wherein $p'$ is zero or one; A is 1,4-cyclohexylene optionally substituted by one or two methyl, ethyl, methoxy or ethoxy groups; and the acarid is a mite of the family Tetranychidae or the family Tarsonemidae.

30. The method according to claim 29 wherein said compound is

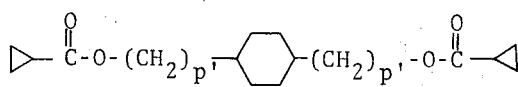

wherein $p'$ is zero and the acarid is a mite of the genus Tetranychus, the genus Bryobia, the genus Oligonychus or the genus Panonychus.

31. The method according to claim 1 wherein said compound is

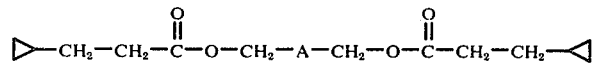

wherein A is 1,4-cyclohexylene and the acarid is a mite of the family Tetranychidae or the family Tarsonemidae.

32. The method according to claim 1 wherein said compound is a compound of the formula:

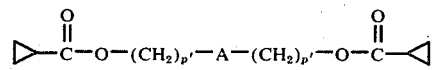

wherein $p'$ is zero or one; A is 1,4-phenylene, 2,7-naphthylene, 4,4'-thiodiphenylene, 4,4'-biphenylene or 4,4'-oxydiphenylene; and the acarid is a mite of the family Tetranychidae or the family Tarsonemidae.

33. The method according to claim 32 wherein said compound is a compound of the formula

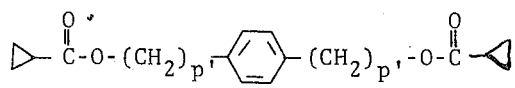

wherein $p'$ is one.

34. The method according to claim 33 wherein the acarid is a mite of the genus Tetranychus, the genus Panonychus, the genus Bryobia or the genus Oligonychus.

35. The method according to claim 1 wherein said compound is a compound of the formula

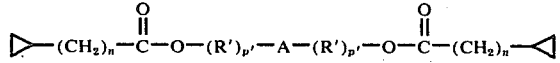

wherein $n$ is two or four; $p'$ is zero or one; A is primary alkylene of eight to sixteen carbon atoms; and the acarid is a mite of the genus Tetranychus, the genus Bryobia, the genus Oligonychus or the genus Panonychus.

36. The method according to claim 35 wherein $n$ is two and A is decamethylene, dodecamethylene or tetradecamethylene.

37. The method according to claim 1 wherein said compound is a compound of the formula:

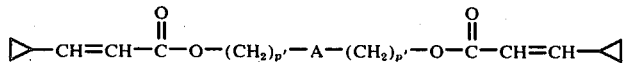

wherein $p'$ is zero or one; A is 1,4-phenylene, 2,7-naphthylene, 4,4'-thiodiphenylene, 4,4'-biphenylene, 4,4'-oxydiphenylene, 1,4-cyclohexylene, primary alkylene of eight to sixteen carbon atoms or primary alkynylene of six to sixteen carbon atoms; and the acarid is a mite of the genus Tetranychus, the genus Bryobia, the genus Oligonychus or the genus Panonychus.

38. The method according to claim 37 wherein A is 1,4-phenylene or 1,4-cyclohexylene.

39. The method according to claim 1 wherein said compound is

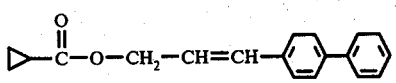

and the acarid is a member of the genus Tetranychus, the genus Bryobia, the genus Oligonychus or the genus Panonychus.

40. The method of claim 1 wherein the compound is tridecyl cyclopropanecarboxylate and the acarid is a mite of the family Tetranychidae or the family Tarsonemidae.

41. The method of claim 1 wherein the compound is pentadecyl cyclopropanecarboxylate and the acarid is a mite of the family Tetranychidae or the family Tarsonemidae.

42. The method of claim 1 wherein the compound is 2-methylhexadecyl cyclopropanecarboxylate and the acarid is a mite of the family Tetranychidae or the family Tarsonemidae.

43. The method of claim 1 wherein said compound is a compound of the formula:

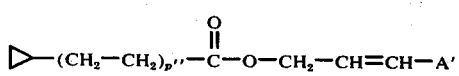

wherein $p''$ is zero or one; A' is 4-methylphenyl, 4-methoxyphenyl, 4-octyloxyphenyl, biphenyl, 4-benzylphenyl, 4-phenoxyphenyl or 4-benzyloxyphenyl; and the acarid is a mite of the family Tetranychidae or the family Tarsonemidae.

44. The method of claim 1 wherein the compound is

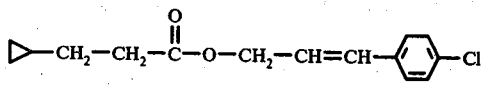

and the acarid is a mite of the family Tetranychidae or the family Tarsonemidae.

45. The method of claim 1 wherein the compound is

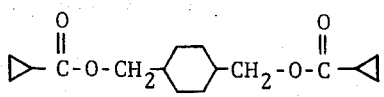

and the acarid is a mite of the genus Tetranychus, the genus Bryobia, the genus Oligonychus or the genus Panonychus.

46. The method of claim 45 wherein the mite is a member of the genus Tetranychus.

47. The method of claim 1 wherein said compound is a compound of the formula:

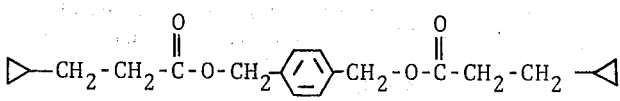

and the acarid is a mite of the genus Tetranychus, the genus Bryobia, the genus Oligonychus or the genus Panonychus.

48. The method of claim 1 wherein said compound is a compound of the formula:

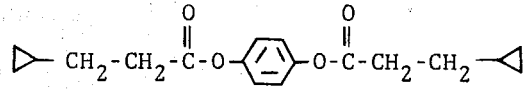

and the acarid is a mite of the genus Tetranychus, the genus Bryobia, the genus Oligonychus or the genus Panonychus.

49. A composition for the control of mites of the order Acarina which comprises a suitable carrier substance and a compound of the formula (I) or (II)

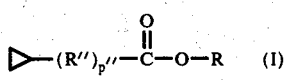

(I)

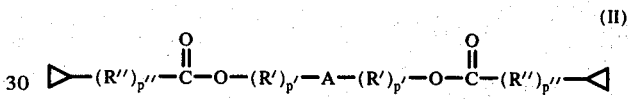

(II)

wherein,

R'' is —CH=CH— or —(CH$_2$)$_n$— in which $n$ is a positive number from one to four;

$p''$ is zero or one;

R is alkyl of ten to twenty-two carbon atoms, alkenyl of ten to twenty-two carbon atoms and having one to three sites of olefinic unsaturation, alkynyl of ten to twenty-two carbon atoms and having one or two sites of acetylenic unsaturation or the group

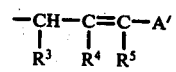

in which A' is phenyl, naphthyl or cycloalkyl of four to eight carbon atoms, each ring being optionally substituted by one or more halogen, alkyl of one to twenty-two carbon atoms, alkoxy of one to fifteen carbon atoms, aryl of six to fourteen carbon atoms, aralkyl of seven to fifteen carbon atoms, aryloxy of six to fourteen carbon atoms or aralkoxy of seven to fifteen carbon atoms groups, and each of R$^3$, R$^4$ and R$^5$ is hydrogen or lower alkyl;

$p'$ is zero or one;

R' is alkylene of one to six carbon atoms or alkenylene of two to six carbon atoms; and A is alkylene of two to twenty carbon atoms, alkenylene of two to twenty carbon atoms and having one to three sites of olefinic unsaturation, alkynylene of two to twenty carbon atoms and having one or two sites of acetylenic unsaturation, arylene of six to twenty carbon atoms optionally substituted by one or two groups selected from alkyl of one to twenty-two carbon atoms, halogen or nitro, or cycloalkylene of four to six carbon atoms optionally substituted by one or two alkyl groups of one to twenty-two carbon atoms or one or two alkoxy groups of one to fifteen carbon atoms; said compound being present in the composition in an ovicidally effective amount or larvicidally effective amount.

50. A composition according to claim 49 wherein the compound is hexadecyl cyclopropanecarboxylate.

51. A composition according to claim 49 wherein the compound is octadecyl cyclopropanecarboxylate.

52. A composition according to claim 49 wherein the compound is 9-octadecenyl cyclopropanecarboxylate.

53. A composition according to claim 49 wherein the compound is a compound of the formula $$\triangleright\!\!-\!\!CH\!\!=\!\!CH\!\!-\!\!\overset{O}{\underset{\|}{C}}\!\!-\!\!OR$$

wherein R is dodecyl, tetradecyl, hexadecyl or octadecyl.

54. A composition according to claim 49 wherein the compound is a compound of the formula $$\triangleright\!\!-\!\!\overset{O}{\underset{\|}{C}}\!\!-\!\!O\!\!-\!\!A\!\!-\!\!O\!\!-\!\!\overset{O}{\underset{\|}{C}}\!\!-\!\!\triangleleft$$

wherein A is primary alkylene of eight to sixteen carbon atoms.

55. A composition according to claim 54 wherein A is dodecylene.

56. A composition according to claim 49 wherein the compound is a compound of the formula:

$$\triangleright\!\!-\!\!\overset{O}{\underset{\|}{C}}\!\!-\!\!O\!\!-\!\!(CH_2)_{p'}\!\!-\!\!A\!\!-\!\!(CH_2)_{p'}\!\!-\!\!O\!\!-\!\!\overset{O}{\underset{\|}{C}}\!\!-\!\!\triangleleft$$

wherein $p'$ is one and A is 1,4-cyclohexylene.

57. A composition according to claim 49 wherein the compound is a compound of the formula:

$$\triangleright\!\!-\!\!\overset{O}{\underset{\|}{C}}\!\!-\!\!O\!\!-\!\!(CH_2)_{p'}\!\!-\!\!\langle\!\!\rangle\!\!-\!\!(CH_2)_{p'}\!\!-\!\!O\!\!-\!\!\overset{O}{\underset{\|}{C}}\!\!-\!\!\triangleleft$$

wherein $p'$ is one.

58. A composition according to claim 49 wherein the compound is 2-methylhexadecyl cyclopropanecarboxylate.

59. A composition according to claim 49 wherein the compound is tetradecyl 3-cyclopropanepropionate.

60. A composition according to claim 49 wherein the compound is the compound of the formula:

$$\triangleright\!\!-\!\!\overset{O}{\underset{\|}{C}}\!\!-\!\!O\!\!-\!\!A\!\!-\!\!O\!\!-\!\!\overset{O}{\underset{\|}{C}}\!\!-\!\!\triangleleft$$

wherein A is 1,4-cyclohexylene.

61. A composition according to claim 49 wherein the compound is the compound of the formula:

$$\triangleright\!\!-\!\!\overset{O}{\underset{\|}{C}}\!\!-\!\!O\!\!-\!\!A\!\!-\!\!O\!\!-\!\!\overset{O}{\underset{\|}{C}}\!\!-\!\!\triangleleft$$

wherein A is 1,4-phenylene.

* * * * *